United States Patent [19]
Howell et al.

[11] Patent Number: 5,772,643
[45] Date of Patent: Jun. 30, 1998

[54] BARBED LUER ADAPTER

[75] Inventors: Glade H. Howell; Timothy J. Erskine, both of Sandy; Christopher N. Cindrich, Provo, all of Utah

[73] Assignee: Becton Dickinson and Company, Franklin Lakes, N.J.

[21] Appl. No.: 608,785

[22] Filed: Feb. 29, 1996

[51] Int. Cl.⁶ ............................................. A61M 5/00
[52] U.S. Cl. .................... 604/283; 604/905; 604/165; 138/155; 285/921; 285/334.2; 285/332.2
[58] Field of Search ..................... 604/280, 283, 604/284, 905, 165; 138/120–122, 155, 109; 285/165, 175, 178, 302, 331–332.1, 334.2, 921, 914

[56] References Cited

U.S. PATENT DOCUMENTS

| | | | |
|---|---|---|---|
| 4,511,163 | 4/1985 | Harris et al. | 285/177 |
| 4,573,978 | 3/1986 | Reilly | 604/240 |
| 4,969,879 | 11/1990 | Lichte | 604/283 |
| 5,360,242 | 11/1994 | Argent | 285/330 |
| 5,360,418 | 11/1994 | Weilbacher et al. | 604/283 |
| 5,393,101 | 2/1995 | Matkovich | 285/3 |
| 5,405,339 | 4/1995 | Kohnen et al. | 604/283 |
| 5,472,242 | 12/1995 | Petersen | 285/93 |
| 5,549,583 | 8/1996 | Sanford et al. | 604/283 |
| 5,569,222 | 10/1996 | Haselhorst et al. | 604/283 |
| 5,611,576 | 3/1997 | Guala | 285/38 |
| 5,611,785 | 3/1997 | Mito et al. | 604/239 |

*Primary Examiner*—Michael Powell Buiz
*Assistant Examiner*—Chalin Smith
*Attorney, Agent, or Firm*—Eric M. Lee

[57] ABSTRACT

The luer adapter of this invention includes a barbed portion having a generally cylindrical distal portion, a generally conical portion, a generally cylindrical portion and a generally outwardly tapered proximal portion. The shape of the barb is substantially the same as the shape of the lumen at the proximal end of a catheter but is slightly larger radially and slightly shorter axially than the proximal portion of the lumen. This ensures that when the barb is inserted into the proximal portion of the lumen the luer adapter is positively locked to the catheter.

11 Claims, 12 Drawing Sheets

BARBED LUER ADAPTER

BACKGROUND OF THE INVENTION

This invention relates to the field of intravenous (IV) catheters. This invention has particular applicability, but is not limited, to peripherally inserted central catheters (PICCs).

Typical peripheral IV catheters are used to gain access to a patient's venous system so the patient can be infused with medicaments, IV solutions or other fluids. The proximal end of such a catheter usually includes a hub that is designed to be connected to a fluid supply line or other medical device such as a syringe or a valve or IV pump. The cannula of these types of catheters are on the order of about one to two inches long. The cannula is either polyurethane or Teflon.

These peripheral IV catheters are typically placed in one of the patient's smaller veins located in the hand or arm with the hub taped to the patient's skin. Since peripheral IV catheters are short, taping the catheter to the patient's skin minimizes the possibility that the catheter will become dislodged from the patient's vein if the patient moves or a clinician manipulates the catheter to connect or disconnect an IV line or other medical device. Peripheral IV catheters may also include extension tubes which extend proximally from the proximal end of the catheter that is inserted into the patient and which include a hub at the proximal end. Such extension tubes can be taped to the patient's skin. Because of biocompatibility issues, typical polyurethane or Teflon peripheral IV catheters are generally kept in a patient only up to about 72 hours. After this time a new peripheral IV catheter must be inserted into the patient.

For certain types of IV therapy, it is important for the distal tip of the catheter to be located in the auxiliary, subclavian or brachiocephalic vein or in the superior vena cava. This is necessary because certain medicaments are extremely harsh. Thus, it is important to have the medicament diluted quickly in a large vein to prevent adverse reaction by the patient. Heretofore, centrally inserted venous access catheters have been used for this type of IV therapy because such catheters can be inserted directly into the large veins of a patient. A drawback of these types of catheters is that placement of such catheters into a patient is considered a surgical procedure which requires a physician.

PICCs are an alternative to centrally inserted, tunneled or implanted venous access devices. PICCs are generally longer than standard peripheral IV catheters. They are inserted into a patient's vein in the arm and advanced through the venous system until the tip is located in the auxiliary, subclavian or brachiocephalic vein or in the superior vena cava. Typical PICCs are formed from silicone or some other biocompatible, soft, flexible polymer. Because of this PICCs can remain in place in a patient for several weeks, months or years. PICCs are thus used for patients needing IV antibiotic therapy for more than seven days, hyperalimentation, chemotherapy, long term IV rehydration or other long term IV therapy.

Many PICCs are currently available. These products work satisfactorily for their intended purpose but could be improved. For example, when the catheter is taped to the patient's skin, the catheter hub, extension tube and any wings on the catheter become a source for abrasion to the patient's skin which can be uncomfortable. In addition, if the patient moves, this movement may exacerbate the discomfort causing pain to the patient. Furthermore, as noted above, typical PICCs are formed from a soft silicone. Therefore, in order to connect an IV fluid line or other medical device to the catheter, a relatively hard adapter must be located at the proximal end of the catheter. Unfortunately, because of the nature of silicone, an adapter cannot simply be glued to the catheter but must be adhered by some other mechanism. Current mechanisms for adhering the adapter to the catheter have not been entirely satisfactory. Finally, it is standard procedure to suture a PICC directly to the patient rather than to tape the catheter down. Current catheters include an orifice through which the suture can be passed to suture the catheter directly to the patient. Unfortunately, these orifices present a point of weakness on the catheter and could result in the sutures tearing completely through a side of the orifice.

SUMMARY OF THE INVENTION

It is therefore an object of this invention to provide an IV catheter that enhances patient comfort.

It is another object of this invention to provide an enhanced mechanism for connecting a catheter to a luer adapter.

It is still another object of this invention to provide a catheter having an enhanced mechanism for suturing or taping the catheter directly to the patient.

The catheter of this invention comprises an elongate tube connected at one end to a low profile extension tube. This low profile extension tube includes a lumen in communication with the lumen of the elongate tube and preferably has an elliptical crosssection with a height to width ratio of between about 1:1.25 to about 1:3. An oval shaped wing may be used with the extension tube to provide a surface that may be used to tape the catheter to the patient's skin. The wing should have a length to width ratio of between about 1:1 to about 1:3. In addition, the wing has a domed cross-section with a ratio of the cross-sectional thickness, edge to center of between about 1:1.5 to about 1:4 to provide sufficient space for the extension tube lumen to pass therethrough. In addition, the oval shaped wing may include a plurality of reinforced suture holes to allow it to be sutured directly to the patient's skin if needed. Finally, the proximal portion of the extension tube of the catheter is flared outwardly to a larger cross-sectional area than the main portion of the extension tube. The lumen along the proximal portion of the extension tube has a unique configuration to mate with a barbed portion of a luer adapter. The unique configuration of the proximal portion of the lumen is substantially the same shape as the barbed portion of the luer adapter. However, the axial dimensions of the proximal portion of the lumen are larger than those of the barbed portion of the luer adapter while the radial dimensions of the proximal portion of the lumen are smaller than those of the barbed portion of the luer adapter. Once the barbed portion of the luer adapter is inserted into the lumen along the proximal portion of the extension tube, the material of the extension tube compresses about the barbed portion of the luer adapter and the configuration of the barb frictionally and mechanically engages the lumen along the proximal portion of the extension tube to effectively lock the luer adapter to the extension tube.

BRIEF DESCRIPTION OF THE DRAWINGS

The above and other objects of this invention will be apparent from the detailed description and drawings in which like parts are referred to by like numbers throughout, and in which.

DETAILED DESCRIPTION OF THE INVENTION

Figure 11:
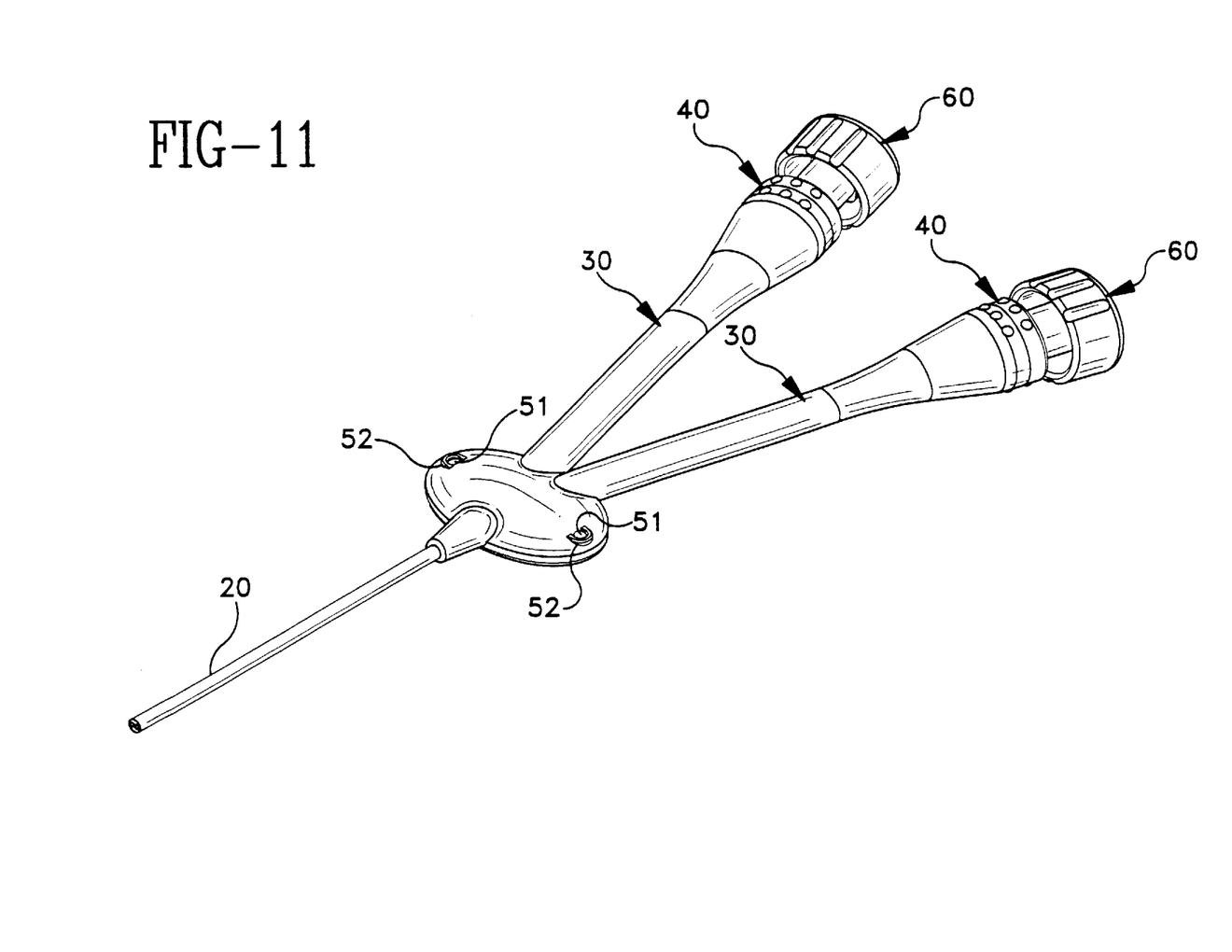
FIG. 11 is a perspective view of a double lumen PICC incorporating the low profile extension tube, wing, barbed luer and guidewire retention device of this invention.
Figure 12:
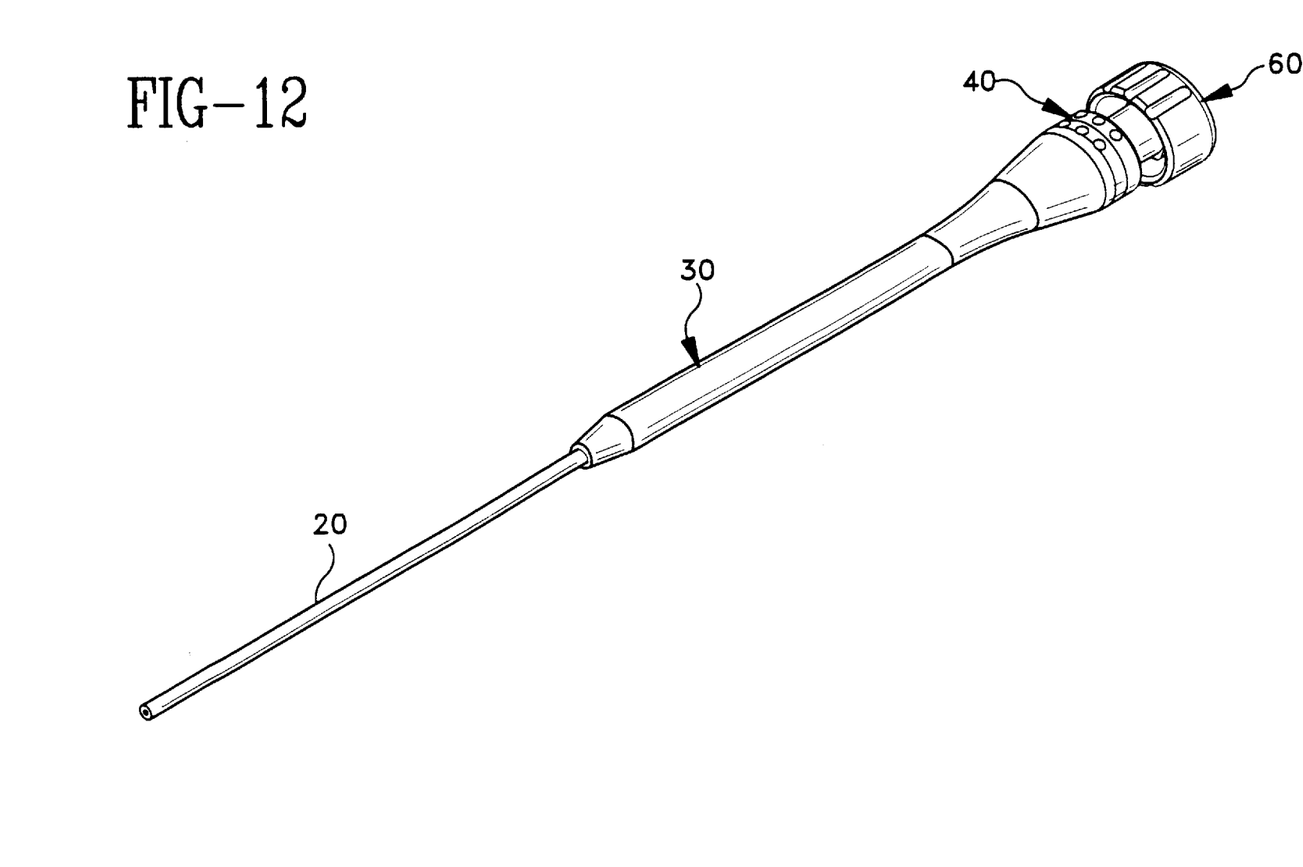
FIG. 12 is a perspective view of a single lumen PICC incorporating the low profile extension tube, the barbed luer and the guidewire retention device of this invention.
Figure 13:
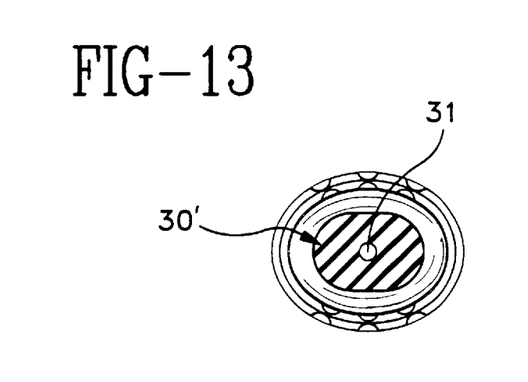
FIG. 13 is a view similar to FIG. 3 showing a second embodiment of the extension tube of this invention.
Figure 14:
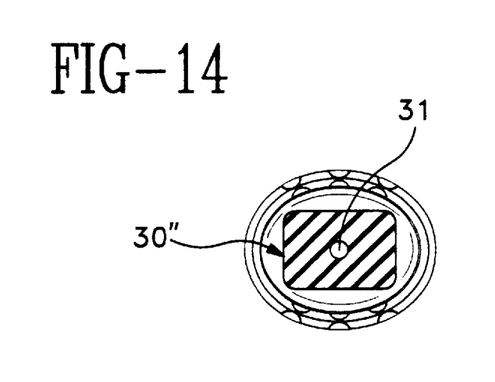
FIG. 14 is a view similar to FIG. 3 showing a third embodiment of the extension tube of this invention.
Figure 15:
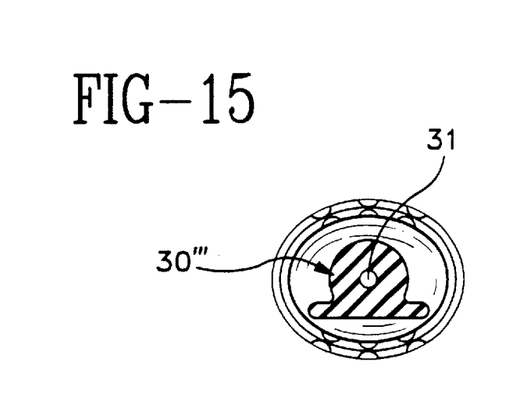
FIG. 15 is a view similar to FIG. 3 showing a fourth embodiment of the extension tube of this invention.
Figure 16:
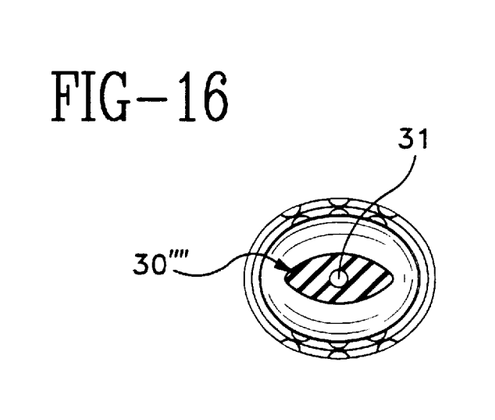
FIG. 16 is a view similar to FIG. 3 showing a fifth embodiment of the extension tube of this invention.
Figure 17:
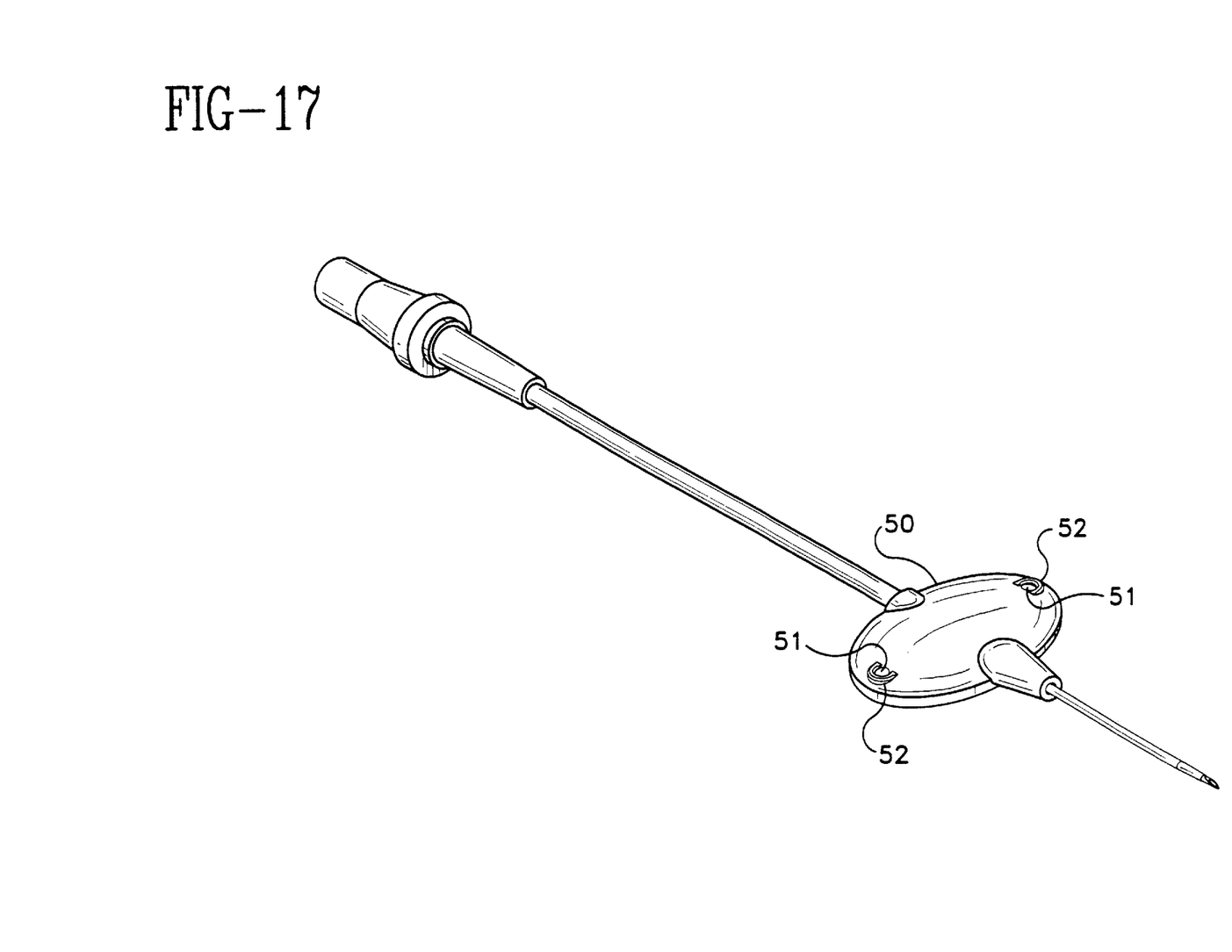
FIG. 17 is a top plan view of a winged catheter with extension tube showing the wing of this invention rotated slightly.
Figure 18:
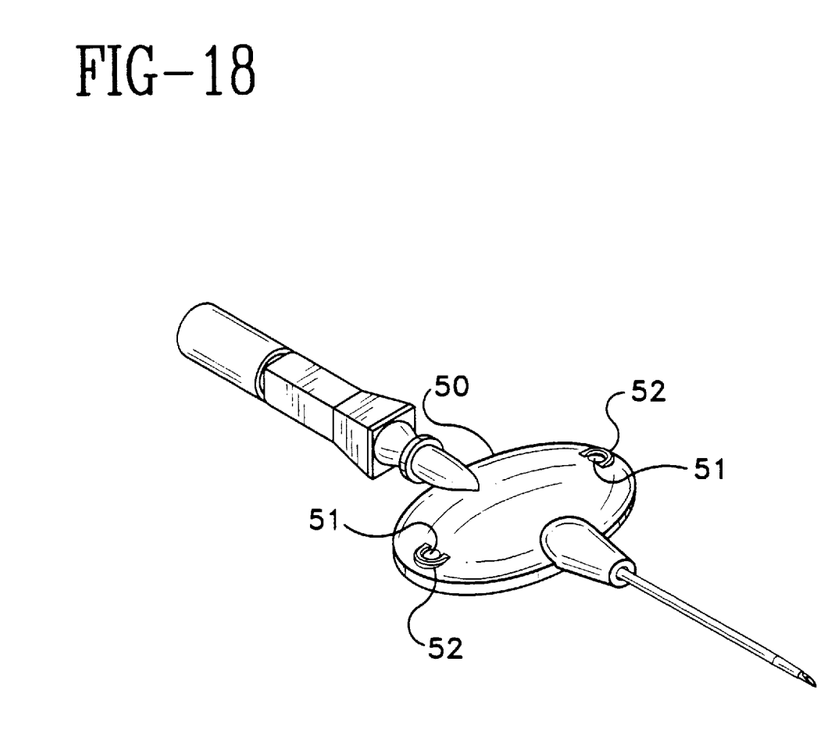
FIG. 18 is a perspective view of a standard IV catheter incorporating the wing of this invention.
Figure 19:
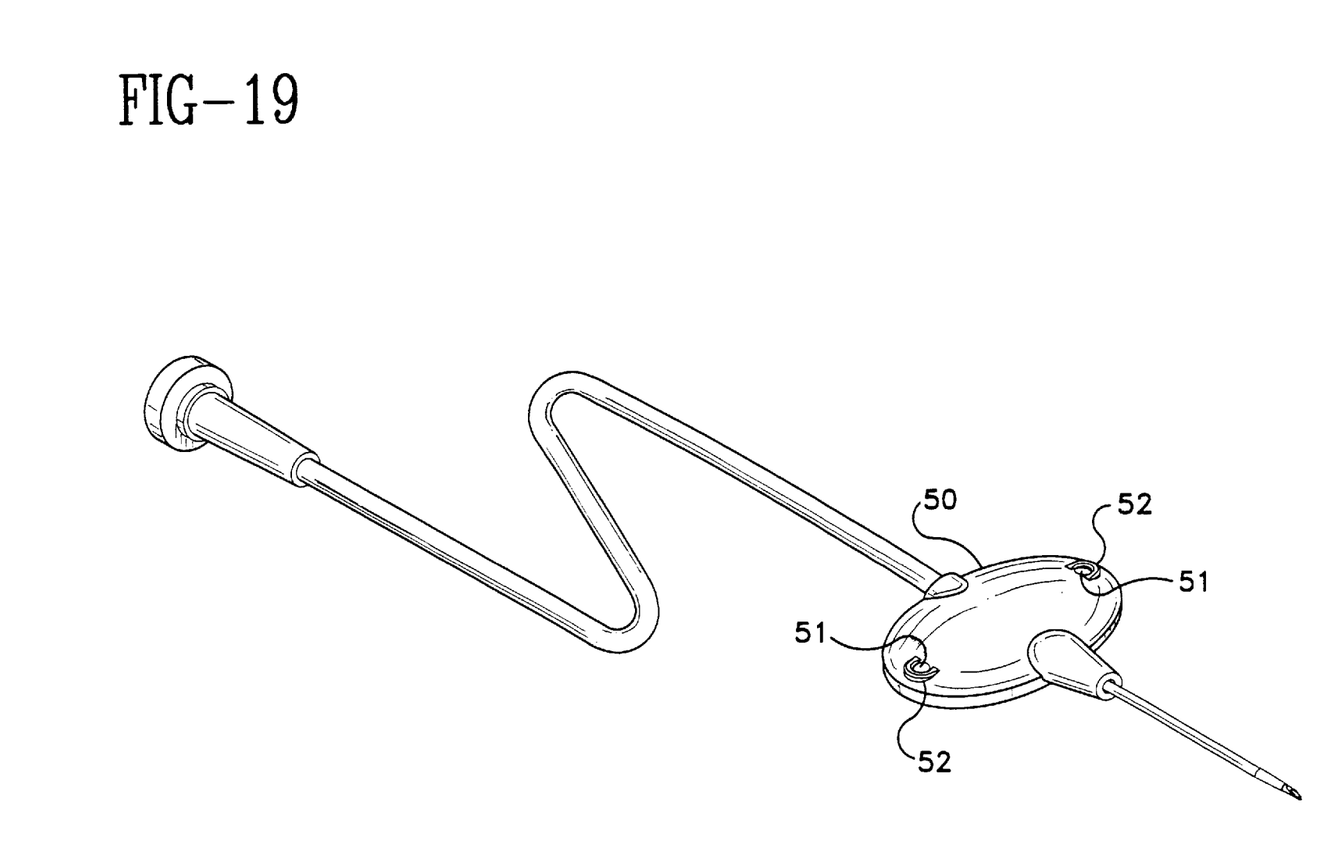
FIG. 19 is a perspective view of a scalp vein needle incorporating the wing of this invention.

The catheter assembly 10 of this invention includes a cannula 20, an extension tube 30, a luer adapter 40 at the proximal end of extension tube 30 and a guidewire retention device 60 located on luer adapter 40. In addition, a wing 50 may be formed integrally with extension tube 30. Cannula 20 has a single lumen extending therethrough. However, cannula 20 may include two lumens extending therethrough. Where cannula 20 includes two lumens, catheter assembly 10 includes two extension tubes. See FIG. 11. It is to be understood that the description of extension tube 30, luer adapter 40 and wing 50 in connection with the single lumen version of this invention applies equally to the extension tubes, luer adapters and wings of the other embodiments of this invention.

Extension tube 30 includes a central lumen 31 extending therethrough and is formed from a soft, flexible material such as silicone. Central lumen 31 is formed in extension tube 30 by molding extension tube 30 in a die with a core pin placed in the die. Preferably a silicone having a durometer of between about 65 Shore A to about 45 Shore A is used. Central lumen 31 has a generally circular cross-section with an inner diameter of about 0.040 inches. Although central lumen 31 preferably has a circular cross-section, this cross-section can be any shape. It is important that central lumen 31 have a wall thickness defined by extension tube 30 of at least about 0.020 inches, preferably about 0.045 inches. Extension tube 30 can be any length. However, the length should be at least long enough to allow flexibility of extension tube 30. The maximum length is based on the ability to mold extension tube 30 and pull a core pin down central lumen 31.

Figure 1:
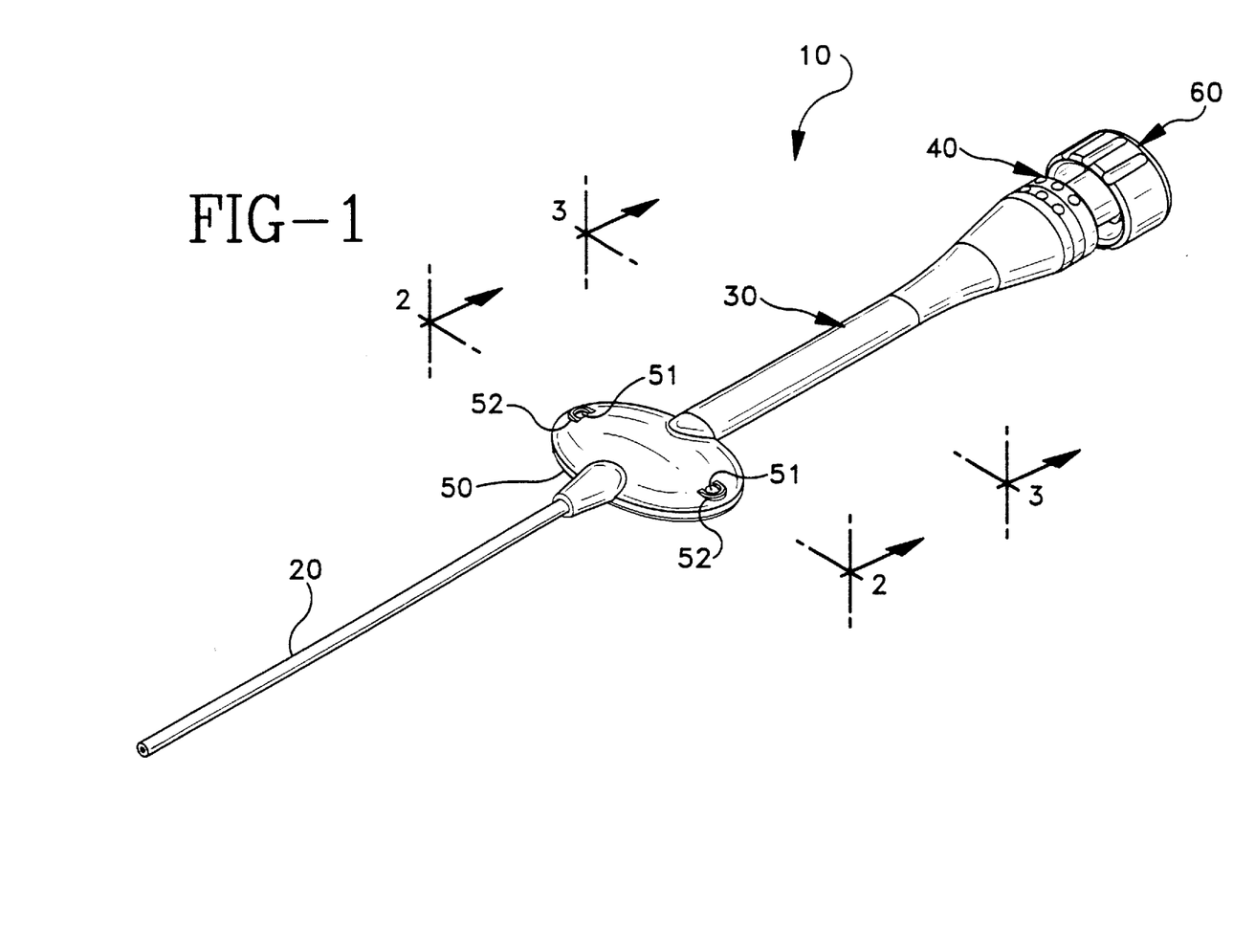
FIG. 1 is a perspective view of a single lumen PICC incorporating the low profile extension tube, wing, barbed luer adapter and guidewire retention device of this invention.
Figure 2:
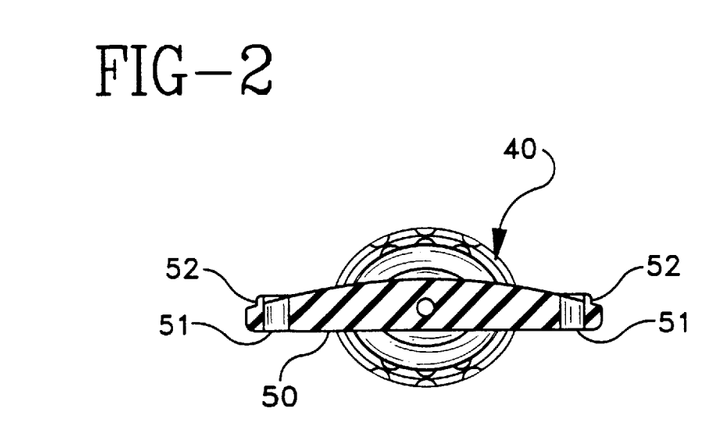
FIG. 2 is a cross-sectional view taken along line 2—2 of FIG. 1.
Figure 3:
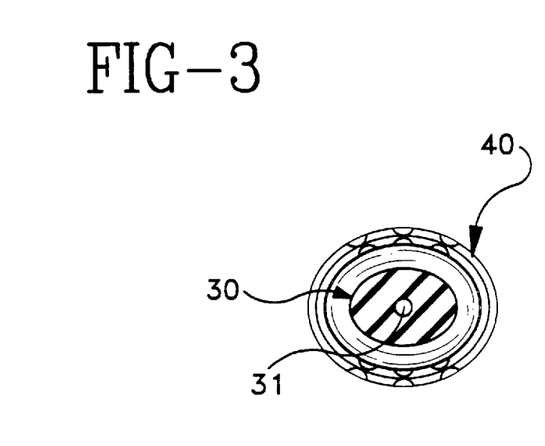
FIG. 3 is a cross-sectional view taken along line 3—3 of FIG. 1.
Figure 4:
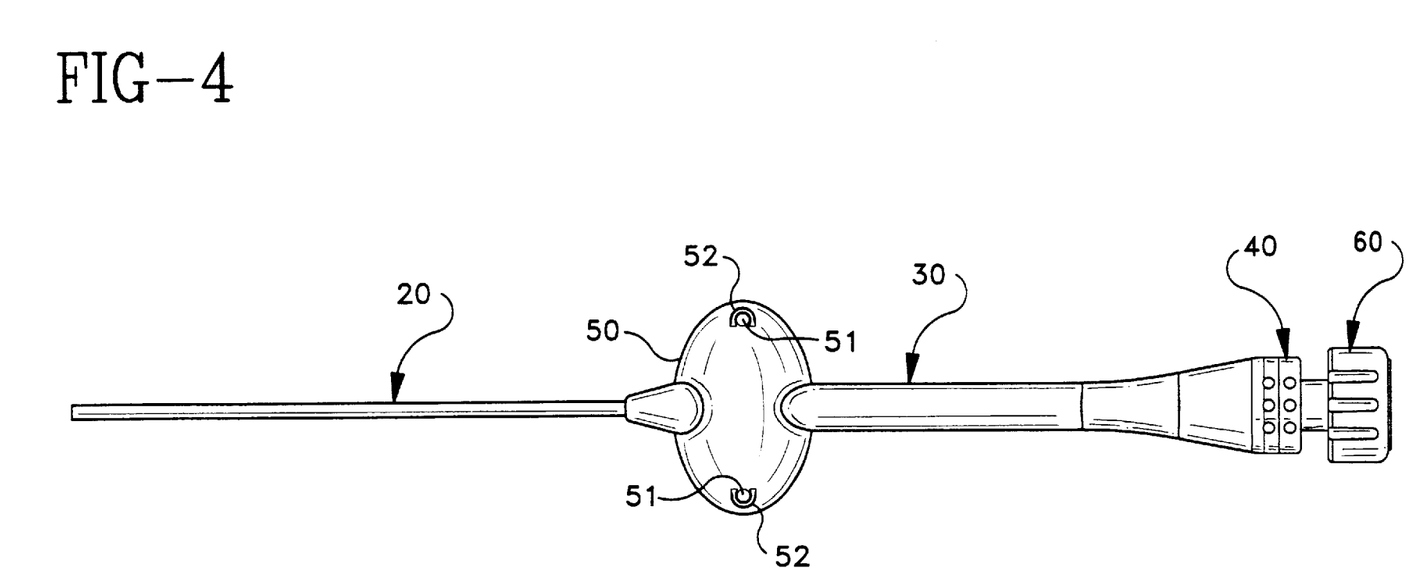
FIG. 4 is a top plan view of a single lumen PICC incorporating the low profile extension tube, wing, barbed luer and guidewire retention device of this invention.
Figure 5:
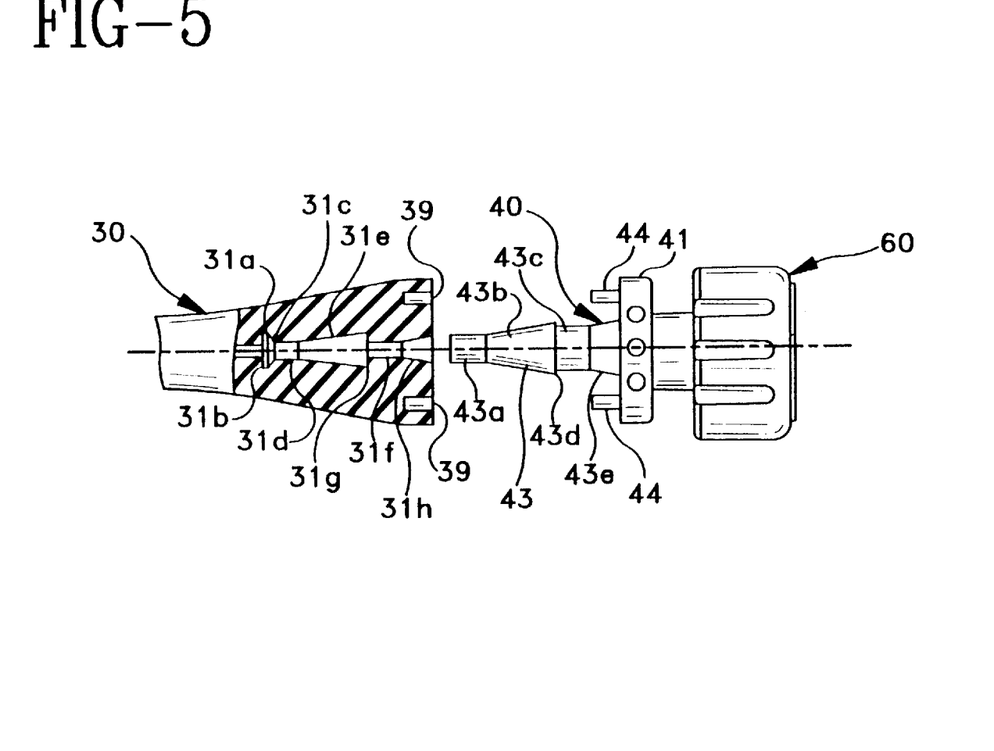
FIG. 5 is a side elevation view partially in cross-section showing the proximal portion of the extension tube before insertion of the barbed luer.

Extension tube 30 has a low profile cross-section which is preferably an oval shape. See FIG. 3. However, any other low profile shape, such as a racetrack shape, a rectangular shape with rounded corners, a circular shape having a flat bottom or an elliptical shape could also be used. See FIGS. 13–16. It is important, however, that the cross-sectional shape for extension tube 30 have a height to width ratio of between about 1:1.25 to about 1:3. Preferably this height to width ratio for extension tube 30 cross-section is 1:1.5. By choosing a height to width ratio in this range, extension tube 30 can flex upwardly more easily than if a circular cross-section is used. Another benefit is that there is less material above lumen 31 in extension tube 30 than in a standard circular extension tube. This facilitates the visualization of fluid flowing through extension tube 30. In addition . even though extension tube 30 has a lower profile than a standard circular extension tube, extension tube 30 has a comparable cross-sectional area. Thus, there is no loss in tensile strength for extension tube 30 as compared to a standard extension tube. Furthermore, this particular configuration for extension tube 30 prevents it from kinking during use.

A wing 50 may be integrally formed along the distal portion of extension tube 30. Alternatively, wing 50 could be separately molded with no lumen therein and then attached to extension tube 30. As can be seen in FIGS. 1, 2, 4, 7, 11 and 17–19, wing 50 has a generally oval shape and a domed cross-section. The oval configuration avoids sharp corners so wing 50 is more comfortable to the patient. As used herein, "oval" also refers to an ellipse, a race track shape, or a rectangle with rounded corners. In addition, its short length provides for greater flexibility while its large width provides adequate surface area for securement to the patient's skin. Wing 50 should have a length to width ratio of between about 1:1 to about 1:3. Preferably the ratio should be about 1:1.5 with a width of about 1.0 inches and a length of about 0.650 inches.

Wing 50 should also have a flat bottom surface and a domed cross section. This domed configuration provides a central portion with enough thickness to allow lumen 31 to extend therethrough. In addition, wing 50 should have a ratio of the cross-sectional thickness, edge to the center, of between about 1:1.5 to about 1:4. Preferably this ratio is about 1:2.3 and wing 50 has a thickness of about 0.15 inches at its center and a thickness of about 0.065 inches at its edge.

Wing 50 may also include one or more suture holes 51 therein. Preferably there is one suture hole 51 on either side of wing 50. Each suture hole 51 is reinforced with a raised ridge 52 along the periphery thereof. Raised ridge 52 provides reinforcement to prevent sutures from tearing through the periphery of wing 50 if wing 50 is sutured directly to a patient's skin. The height and width of raised ridge 52 are chosen to reinforce the thinner cross-sectional area of wing 50 under raised ridge 52. Preferably raised ridge 52 has a height and width about equal to the height of wing 50 under raised ridge 52.

The cross section of extension tube 30 increases gradually along its proximal portion. In addition, the cross section of central lumen 31 changes along the proximal portion of extension tube 30. The main portion of central lumen 31 preferably has an inner diameter of about 0.040 inches. Central lumen 31 has a portion 31a with an increased diameter adjacent to the main portion of central lumen 31 so as to present a first shoulder 31b in central lumen 31. This portion 31a of central lumen 31 preferably has an inner diameter of about 0.080 inches. Continuing in the proximal direction the cross-section of central lumen 31 tapers inwardly along portion 31c to a portion 31d of constant diameter and then outwardly in a generally conical shape along portion 31e. Thereafter, the cross-section of central lumen 31 has a reduced constant diameter along portion 31f so as to present a second shoulder 31g in central lumen 31. The most proximal portion 31h tapers outwardly to the proximal end of extension tube 30. This cross section along the proximal portion of central lumen 31 is important in order to allow luer adapter 40 to be connected to the proximal end of extension tube 30. In addition, the proximal portion of extension tube 30 can include one or more alignment holes 39.

Luer adapter 40 is formed from a hard durable material such as polypropylene or polycarbonate. Luer adapter 40 is formed with a flange 41 having a cross section that matches the cross section of extension tube 30 at its proximal end. The proximal portion of luer adapter 40 is formed into a standard female luer connector 42. The distal portion of luer adapter 40 includes a barb 43 and may include one or more alignment pins 44 or 44'. Alignment pins 44 may be generally cylindrical or alignment pins 44' may include a hooked end.

Barb 43 defines a lumen 45 extending therethrough. Barb 43 has a cross-section that is substantially the same as but slightly larger radially and slightly shorter axially than the cross-section of the proximal portion of central lumen 31. The distal portion 43a of barb 43 is substantially cylindrical. The next portion 43b flares outwardly in the proximal direction so it has a generally conical shape. The next portion 43c of barb 43 is generally cylindrical with a smaller diameter than the proximal end of portion 43b to provide a shoulder 43d along barb 43. Finally, the proximal portion 43e of barb 43 tapers slightly outwardly. The diameter along portions 31d, 31e, 31f and 31h of central lumen 31 are between about 25% to about 90%, preferably about 60% smaller than the diameter along portions 43a, 43b, 43c and 43e of barb 43 when extension tube 30 is in the unstressed state. Preferably portions 43c and 43e combined are about 0.030 inches shorter than portion 31f and 31h, and portion 43b and distal portion 43a combined are about 0.025 inches shorter than portion 31a, 31c, 31d and 31e when extension tube 30 is in the unstressed state. Shoulder 43d defines an annulus that has a width of between about 0.010 inches to about 0.030 inches, preferably about 0.018 inches. In addition, the diameter of flange 41 is larger than the diameter of the proximal end of extension tube 30 in the unstressed state.

Figure 6:
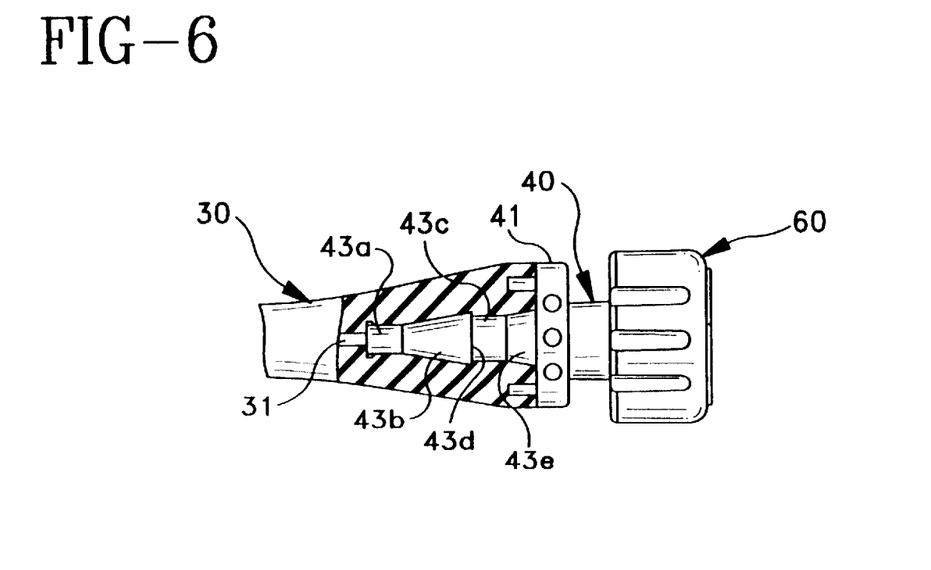
FIG. 6 is a side elevation view partially in cross-section showing the proximal portion of the extension tube with the barbed luer inserted therein.
Figure 7:
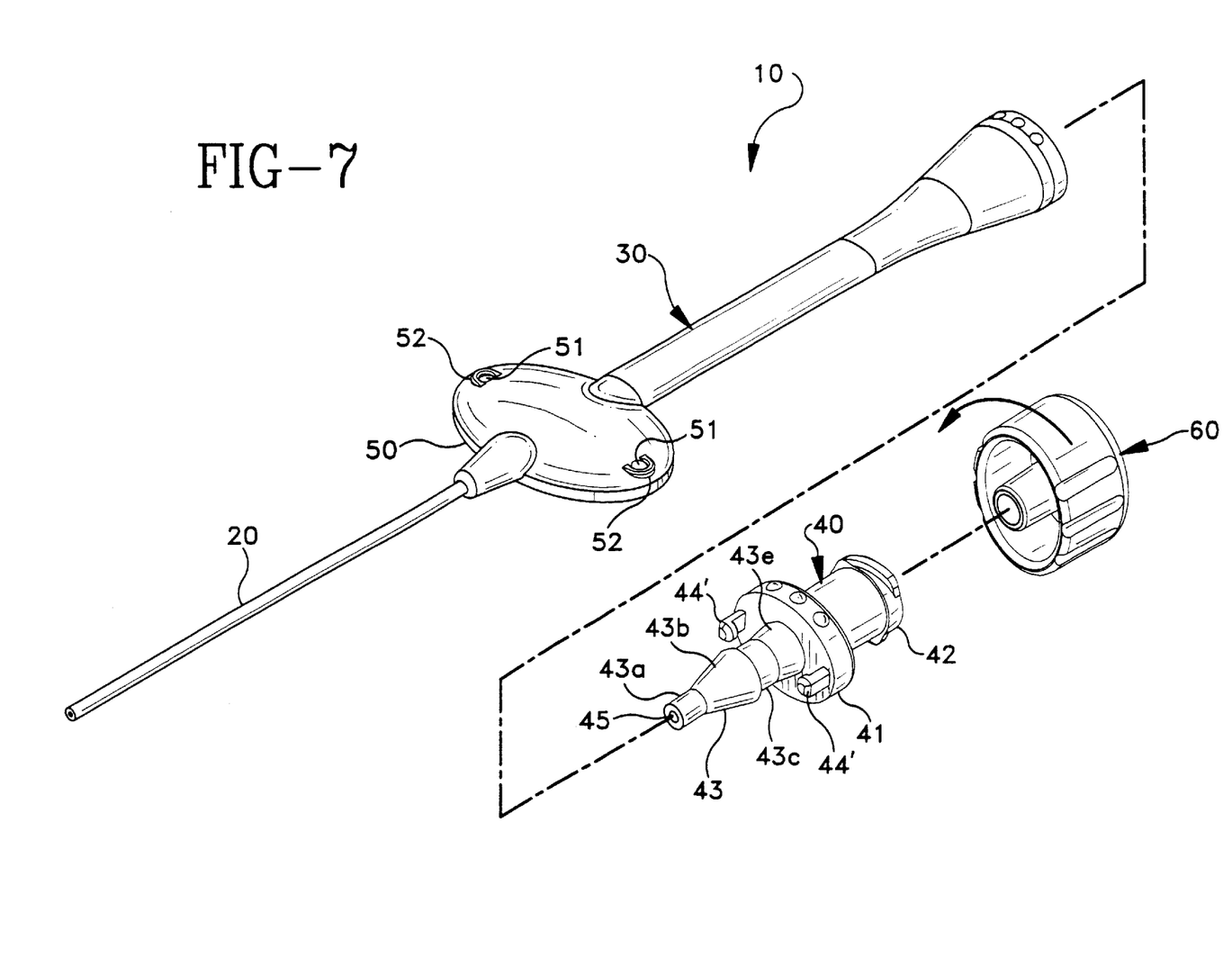
FIG. 7 is an exploded perspective view of a single lumen PICC incorporating the low profile extension tube, the wing, the barbed luer and the guidewire retention device of this invention.
Figure 8:
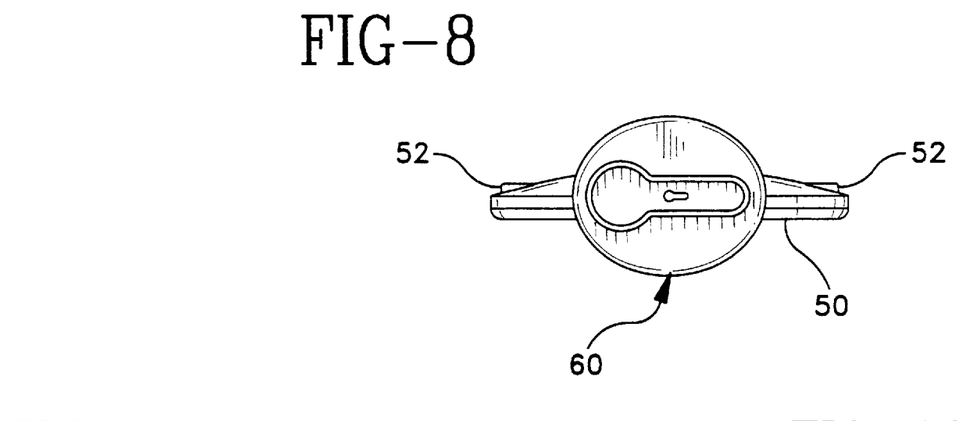
FIG. 8 is a rear end elevation view of the PICC shown in FIG. 1.

When barb 43 is fully inserted into the proximal portion of central lumen 31, lumen 45 is aligned with central lumen 31. Portion 31c in conjunction with the diameter of portion 31a being about equal to the diameter of portion 43a ensure that the material of extension tube 30 does not stretch in the area of first shoulder 31b so that central lumen 31 remains aligned with lumen 45. See FIG. 6. Alternatively, the portion of central lumen 31 adjacent to first shoulder 31b could decrease in diameter so that when barb 43 is inserted into and thereby stretches the proximal portion of lumen 31, central lumen 31 will be aligned with lumen 45. In addition, the distal end of barb 43 abuts shoulder 31b to prevent any fluid from collecting between barb 43 and central lumen 31 and to prevent turbulence when fluid flows from luer adapter 40 into central lumen 31. See FIG. 6. And the outside surface of flange 41 is contiguous with the outside surface of extension tube 30.

Because extension tube 30 is preferably formed from silicone, the diameter of the proximal portion of extension tube 30 is stretched when barb 43 is inserted into central lumen 31. Compressive forces exerted on barb 43 caused by the different dimensions of the proximal portion of central lumen 31 maintain the two joined without the need for other attachment mechanisms. The configuration and dimension of barb 43 and central lumen 31 ensure that luer adapter 40 remains fixed to extension tube 30 during use because of mechanical and frictional forces. If a harder silicone is used for extension tube 30 then the diameter along the proximal portion of central lumen 31, when extension tube 30 is in the unstressed state, can be smaller because less compression will be needed to retain barb 43 in central lumen 31. When luer adapter 40 is inserted into the proximal portion of extension tube 30, barb 43 engages the walls of central lumen 31 at the proximal portion of extension tube 30.

Alignment pins 44 or 44' fit within alignment holes 39 formed in the proximal end of extension tube 30. The use of alignment pins 44 or 44' and alignment holes 39 prevent rotation of luer adapter 40 with respect to extension tube 30.

Figure 9:
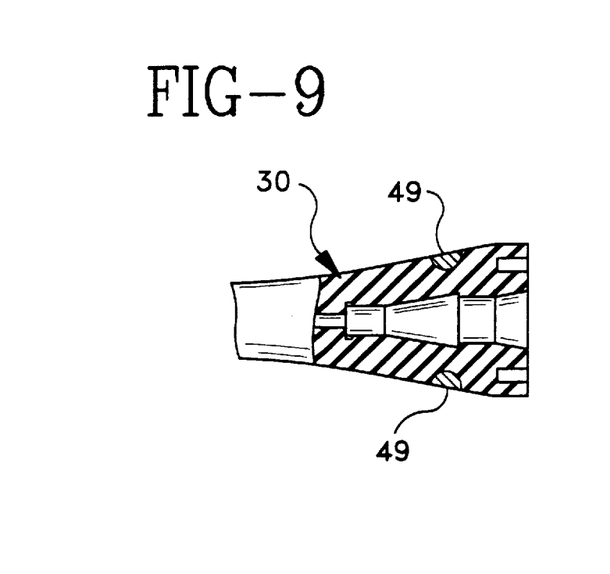
FIG. 9 is a side elevational view partially in cross-section showing another embodiment of the proximal portion of the extension tube.
Figure 10:
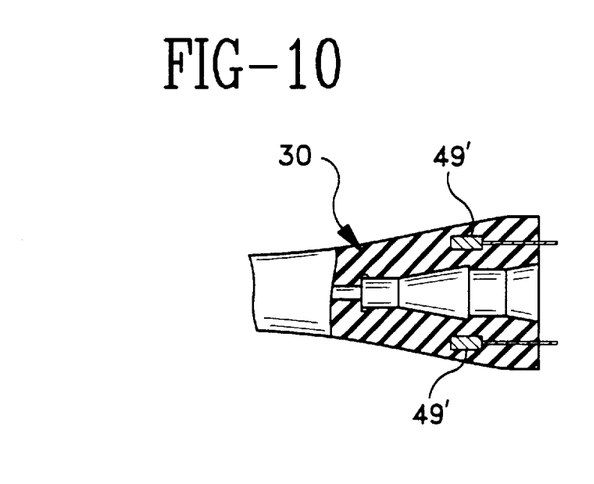
FIG. 10 is a side elevational view partially in cross-section showing yet another embodiment of the proximal portion of the extension tube.

In order to strengthen the bond between extension tube 30 and luer adapter 40 a rigid circumferential band 49 can be placed around the outside of extension tube 30 so band 49 is adjacent to second shoulder 31g. See FIG. 9. Band 49 radially compresses extension tube 30 about barb 43 greatly increasing the force necessary to remove luer adapter 40 from extension tube 30. Alternatively, band 49' can be insert molded into extension tube 30 so band 49' is located adjacent to second shoulder 31g. See FIG. 10. In this embodiment, band 49' radially compresses extension tube 30 about barb 43. In addition, band 49' can have fittings that either bond to or snap fit on luer adapter 40 making it virtually impossible to remove luer adapter 40 from extension tube 30 without severely damaging extension tube 30.

Thus, it is seen that a catheter is provided that enhances patient comfort, that has an enhanced mechanism for bonding to a luer adapter and for suturing the catheter directly to the patient.

We claim:

1. A luer adapter, comprising:

a proximal generally tubular portion having a proximal end and a distal end;

a flange having a proximal face and a distal face with the proximal face affixed to the distal end of the proximal generally tubular portion; and a barbed portion affixed to the distal face of the flange, wherein the barb has a generally cylindrical distal portion with a proximal end, a generally conical portion having a proximal end and a distal end affixed to the proximal end of the generally cylindrical distal portion, a generally cylindrical intermediate portion having a proximal end and a distal end affixed to the proximal end of the generally conical portion, and an outwardly tapered proximal portion having a proximal end affixed to the distal face of the flange and a distal end with a diameter substantially equal to a diameter of the proximal end of the generally cylindrical intermediate portion affixed to the proximal end of the generally cylindrical intermediate portion.

2. The luer adapter of claim 1 further comprising a shoulder defined between the generally conical portion and the generally cylindrical intermediate portion wherein the shoulder defines an annulus having a width between about 0.010 inches and about 0.030 inches.

3. The luer adapter of claim 1 further comprising at least one anti-rotation pin affixed to the distal face of the flange.

4. The luer adapter of claim 3 wherein the anti-rotation pin has a distal portion with a hooked configuration.

5. A catheter and luer adapter assembly, comprising:

a catheter having a tubular proximal portion with a proximal end and a lumen extending therethrough, the lumen having a generally constant diameter along a major part of its length and a proximal portion with a cross-section of varying diameter including a first section having a substantially constant diameter abutting the major part of the lumen and having a diameter larger than the major part of the lumen to define a first shoulder therebetween, a tapered second section abutting the first section and having a diameter that decreases in the proximal direction, a third section having a substantially constant diameter abutting the second section, a fourth section abutting the third section having a diameter that increases in the proximal direction, and a fifth section abutting the fourth section and having a diameter adjacent to the fourth section less than the diameter of the fourth section at its proximal end to define a second shoulder therebetween; and a luer adapter having a flange and a barb connected to the flange, the barb having a generally cylindrical distal portion with a distal end and a proximal end, a generally conical portion having a length, a proximal end and a distal end affixed to the proximal end of the distal portion, and a proximal portion having a length, a proximal end affixed to the flange and a distal end affixed to the proximal end of the generally conical portion to define a barb shoulder therebetween wherein the barb is disposed in the proximal portion of the lumen so the distal end of the barb abuts the first shoulder and the barb shoulder abuts the second shoulder and the flange abuts the proximal end of the catheter.

6. The catheter and luer adapter assembly of claim 5 wherein the barb shoulder defines an annulus having a width of between about 0.010 inches and about 0.030 inches.

7. The catheter and luer adapter assembly of claim 5 wherein the fifth section of the lumen has a length about 0.030 inches greater than the length of the proximal portion of the barb when the proximal portion of the lumen is not stressed.

8. The catheter and luer adapter assembly of claim 5 wherein the third section and the fourth section of the lumen have a combined length about 0.025 inches greater than the combined length of the generally cylindrical distal portion and the conical portion of the barb when the proximal portion of the lumen is not stressed.

9. The catheter and luer adapter assembly of claim 5 wherein the barb shoulder defines an annulus having a width of between about 0.010 inches and about 0.030 inches.

10. The catheter and luer adapter assembly of claim 9 wherein the fifth section of the lumen has a length about 0.030 inches greater than the length of the proximal portion of the barb when the proximal portion of the lumen is not stressed.

11. The catheter and luer adapter assembly of claim 10 wherein the third section and the fourth section of the lumen have a combined length about 0.025 inches greater than the combined length of the generally cylindrical distal portion and the conical portion of the barb when the proximal portion of the lumen is not stressed.

* * * * *